US010576182B2

(12) United States Patent
Cruise et al.

(10) Patent No.: US 10,576,182 B2
(45) Date of Patent: Mar. 3, 2020

(54) RADIOACTIVE LIQUID EMBOLIC

(71) Applicant: MicroVention, Inc., Aliso Viejo, CA (US)

(72) Inventors: Gregory M. Cruise, Rancho Santa Margarita, CA (US); Xinping Wu, Aliso Viejo, CA (US); Matthew J. Fitz, Aliso Viejo, CA (US); Yue Wu, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 0 days.

(21) Appl. No.: 16/155,763

(22) Filed: Oct. 9, 2018

(65) Prior Publication Data

US 2019/0105425 A1  Apr. 11, 2019

Related U.S. Application Data

(60) Provisional application No. 62/569,941, filed on Oct. 9, 2017.

(51) Int. Cl.
*A61L 24/00* (2006.01)

(52) U.S. Cl.
CPC ......... *A61L 24/0005* (2013.01); *A61L 24/001* (2013.01); *A61L 24/0015* (2013.01); *A61L 2300/428* (2013.01); *A61L 2300/44* (2013.01); *A61L 2400/12* (2013.01); *A61L 2430/36* (2013.01)

(58) Field of Classification Search
None
See application file for complete search history.

(56) References Cited

U.S. PATENT DOCUMENTS

| | | |
|---|---|---|
| 3,852,341 A | 12/1974 | Bjork et al. |
| 4,406,878 A | 9/1983 | Boer et al. |
| 5,580,568 A | 12/1996 | Greff et al. |
| 5,667,767 A | 9/1997 | Greff et al. |
| 5,695,480 A | 12/1997 | Evans et al. |
| 5,702,361 A | 12/1997 | Evans et al. |
| 5,755,658 A | 5/1998 | Wallace et al. |
| 5,823,198 A | 10/1998 | Jones et al. |
| 5,830,178 A | 11/1998 | Jones et al. |
| 5,851,508 A | 12/1998 | Greff et al. |
| 5,894,022 A | 4/1999 | Ji et al. |
| 6,004,573 A | 12/1999 | Rathi et al. |
| 6,015,541 A | 1/2000 | Greff et al. |
| 6,017,977 A | 1/2000 | Evans et al. |
| 6,037,366 A | 3/2000 | Krall et al. |
| 6,040,408 A | 3/2000 | Koole |
| 6,051,607 A | 4/2000 | Greff et al. |
| 6,146,373 A | 11/2000 | Cragg et al. |
| 6,281,263 B1 | 8/2001 | Evans et al. |
| 6,303,100 B1 | 10/2001 | Ricci et al. |
| 6,333,020 B1 | 12/2001 | Wallace et al. |
| 6,335,384 B1 | 1/2002 | Evans et al. |
| 6,342,202 B1 | 1/2002 | Evans et al. |
| 6,394,945 B1 | 5/2002 | Chan et al. |
| 6,454,738 B1 | 9/2002 | Tran et al. |
| 6,475,477 B1 | 11/2002 | Kohn et al. |
| 6,503,244 B2 | 1/2003 | Hayman |
| 6,511,468 B1 | 1/2003 | Cragg et al. |
| 6,511,472 B1 | 1/2003 | Hayman et al. |
| 6,531,111 B1 | 3/2003 | Whalen et al. |
| 6,558,367 B1 | 5/2003 | Cragg et al. |
| 6,562,362 B1 | 5/2003 | Bae et al. |
| 6,565,551 B1 | 5/2003 | Jones et al. |
| 6,569,190 B2 | 5/2003 | Whalen et al. |
| 6,599,448 B1 | 7/2003 | Ehrhard et al. |
| 6,602,269 B2 | 8/2003 | Wallace et al. |
| 6,610,046 B1 * | 8/2003 | Usami ............... A61M 25/0052 600/585 |
| 6,616,591 B1 | 9/2003 | Teoh et al. |
| 6,623,450 B1 | 9/2003 | Dutta et al. |
| 6,645,167 B1 | 11/2003 | Whalen, II et al. |
| 6,699,222 B1 | 3/2004 | Jones et al. |
| 6,756,031 B2 | 6/2004 | Evans et al. |
| 6,759,028 B2 | 7/2004 | Wallace et al. |
| 6,962,689 B2 | 11/2005 | Whalen et al. |
| 6,964,657 B2 | 11/2005 | Cragg et al. |
| 6,979,464 B2 | 12/2005 | Gutowska |
| 7,018,365 B2 | 3/2006 | Strauss et al. |
| 7,070,607 B2 | 7/2006 | Murayama et al. |
| 7,083,643 B2 | 8/2006 | Whalen et al. |
| 7,138,106 B2 | 11/2006 | Evans et al. |
| 7,374,568 B2 | 5/2008 | Whalen et al. |
| 7,459,142 B2 | 12/2008 | Greff |
| 7,476,648 B1 | 1/2009 | Tabata et al. |
| 7,507,229 B2 | 3/2009 | Hewitt et al. |
| 7,507,394 B2 | 3/2009 | Whalen et al. |
| 7,776,063 B2 | 8/2010 | Sawhney et al. |
| 7,790,141 B2 | 9/2010 | Pathak et al. |
| 7,838,699 B2 | 11/2010 | Schwarz et al. |
| 7,976,527 B2 | 7/2011 | Cragg et al. |
| 8,066,667 B2 | 11/2011 | Hayman et al. |
| 8,235,941 B2 | 8/2012 | Hayman et al. |

(Continued)

FOREIGN PATENT DOCUMENTS

| | | |
|---|---|---|
| CA | 2551373 C | 6/2014 |
| CN | 101513542 B | 8/2012 |

(Continued)

OTHER PUBLICATIONS

Argawal et al., Chitosan-based systems for molecular imaging. Advanced Drug Delivery Reviews, 62:42-48 (2010).

(Continued)

*Primary Examiner* — James W Rogers
(74) *Attorney, Agent, or Firm* — K&L Gates LLP; Louis C. Cullman; Benjamin D. Heuberger

(57) ABSTRACT

Liquid embolic preparations and medical treatment methods of using those preparations are described. In some embodiments, the preparations or solutions can transition from a liquid to a solid for use in the embolization. The preparations can include biocompatible polymers with covalently bound radioactive iodine isotopes.

20 Claims, No Drawings

(56) References Cited

U.S. PATENT DOCUMENTS

| | | |
|---|---|---|
| 8,454,649 B2 | 6/2013 | Cragg et al. |
| 8,486,046 B2 | 7/2013 | Hayman et al. |
| 8,492,329 B2 | 7/2013 | Shemesh et al. |
| 8,685,367 B2 | 4/2014 | Brandom et al. |
| 9,351,993 B2 | 5/2016 | Cruise et al. |
| 9,434,800 B2 | 9/2016 | Chevalier et al. |
| 9,655,989 B2 | 5/2017 | Cruise et al. |
| 2001/0022962 A1 | 9/2001 | Greff et al. |
| 2001/0024637 A1 | 9/2001 | Evans et al. |
| 2001/0033832 A1 | 10/2001 | Wallace et al. |
| 2001/0036451 A1 | 11/2001 | Goupil et al. |
| 2001/0046518 A1 | 11/2001 | Sawhney |
| 2002/0026234 A1 | 2/2002 | Li et al. |
| 2002/0042378 A1 | 4/2002 | Reich et al. |
| 2003/0021762 A1 | 1/2003 | Luthra et al. |
| 2003/0040733 A1 | 2/2003 | Cragg et al. |
| 2003/0100942 A1 | 5/2003 | Ken et al. |
| 2003/0211083 A1 | 11/2003 | Vogel et al. |
| 2003/0232198 A1 | 12/2003 | Lamberti et al. |
| 2004/0024098 A1 | 2/2004 | Mather et al. |
| 2004/0091425 A1 | 5/2004 | Boschetti |
| 2004/0091543 A1 | 5/2004 | Bell et al. |
| 2004/0157082 A1 | 8/2004 | Ritter et al. |
| 2004/0158282 A1 | 8/2004 | Jones et al. |
| 2004/0161547 A1 | 8/2004 | Carlson et al. |
| 2004/0209998 A1 | 10/2004 | De Vries |
| 2004/0224864 A1 | 11/2004 | Patterson et al. |
| 2004/0228797 A1 | 11/2004 | Bein et al. |
| 2004/0241158 A1 | 12/2004 | McBride et al. |
| 2005/0003010 A1 | 1/2005 | Cohen et al. |
| 2005/0008610 A1 | 1/2005 | Schwarz et al. |
| 2005/0106119 A1 | 5/2005 | Brandom et al. |
| 2005/0123596 A1 | 6/2005 | Kohane et al. |
| 2005/0143484 A1 | 6/2005 | Fang et al. |
| 2005/0175709 A1 | 8/2005 | Baty et al. |
| 2005/0196449 A1 | 9/2005 | DiCarlo et al. |
| 2005/0226935 A1 | 10/2005 | Kamath et al. |
| 2005/0244504 A1 | 11/2005 | Little et al. |
| 2005/0265923 A1 | 12/2005 | Toner et al. |
| 2006/0008499 A1 | 1/2006 | Hudak |
| 2006/0067883 A1 | 3/2006 | Krom et al. |
| 2006/0069168 A1 | 3/2006 | Tabata et al. |
| 2006/0088476 A1 | 4/2006 | Harder et al. |
| 2006/0233854 A1 | 10/2006 | Seliktar et al. |
| 2007/0026039 A1 | 2/2007 | Drumheller et al. |
| 2007/0196454 A1 | 8/2007 | Stockman et al. |
| 2007/0208141 A1 | 9/2007 | Shull et al. |
| 2007/0224234 A1 | 9/2007 | Steckel et al. |
| 2007/0231366 A1 | 10/2007 | Sawhney et al. |
| 2007/0237741 A1 | 10/2007 | Figuly et al. |
| 2007/0248567 A1 | 10/2007 | Pathak et al. |
| 2008/0019921 A1 | 1/2008 | Zhang |
| 2008/0038354 A1 | 2/2008 | Slager et al. |
| 2008/0039890 A1 | 2/2008 | Matson et al. |
| 2008/0114277 A1 | 5/2008 | Ambrosio et al. |
| 2008/0214695 A1 | 9/2008 | Pathak et al. |
| 2008/0226741 A1 | 9/2008 | Richard |
| 2008/0243129 A1 | 10/2008 | Steffen et al. |
| 2008/0269874 A1 | 10/2008 | Wang et al. |
| 2008/0281352 A1 | 11/2008 | Ingenito et al. |
| 2009/0041850 A1 | 2/2009 | Figuly |
| 2009/0048659 A1 | 2/2009 | Weber et al. |
| 2009/0054535 A1 | 2/2009 | Figuly et al. |
| 2009/0093550 A1 | 4/2009 | Rolfes et al. |
| 2009/0117033 A1 | 5/2009 | O'Gara |
| 2009/0117070 A1 | 5/2009 | Daniloff et al. |
| 2009/0181068 A1 | 7/2009 | Dunn |
| 2009/0186061 A1 | 7/2009 | Griguol et al. |
| 2009/0215923 A1 | 8/2009 | Carnahan et al. |
| 2009/0221731 A1 | 9/2009 | Vetrecin et al. |
| 2009/0259302 A1 | 10/2009 | Trollsas et al. |
| 2010/0010159 A1 | 1/2010 | Belcheva |
| 2010/0023112 A1 | 1/2010 | Borck et al. |
| 2010/0036491 A1 | 2/2010 | He et al. |
| 2010/0042067 A1 | 2/2010 | Koehler |
| 2010/0049165 A1 | 2/2010 | Sutherland et al. |
| 2010/0080788 A1 | 4/2010 | Barnett et al. |
| 2010/0086678 A1 | 4/2010 | Arthur et al. |
| 2010/0158802 A1* | 6/2010 | Hansen .................. A61K 45/06 424/1.49 |
| 2010/0247663 A1 | 9/2010 | Day et al. |
| 2010/0256777 A1 | 10/2010 | Datta et al. |
| 2010/0303804 A1 | 12/2010 | Liska et al. |
| 2011/0008406 A1 | 1/2011 | Altman et al. |
| 2011/0008442 A1 | 1/2011 | Zawko et al. |
| 2011/0020236 A1 | 1/2011 | Bohmer et al. |
| 2011/0071495 A1 | 3/2011 | Tekulve |
| 2011/0091549 A1 | 4/2011 | Blaskovich et al. |
| 2011/0182998 A1 | 7/2011 | Reb et al. |
| 2011/0190813 A1 | 8/2011 | Brownlee et al. |
| 2011/0202016 A1 | 8/2011 | Zugates et al. |
| 2012/0041481 A1 | 2/2012 | Daniloff et al. |
| 2012/0059394 A1 | 3/2012 | Brenner et al. |
| 2012/0114589 A1 | 5/2012 | Rolfes-Meyering et al. |
| 2012/0156164 A1 | 6/2012 | Park et al. |
| 2012/0164100 A1 | 6/2012 | Li et al. |
| 2012/0184642 A1 | 7/2012 | Baiting et al. |
| 2012/0238644 A1 | 9/2012 | Gong et al. |
| 2012/0244198 A1 | 9/2012 | Malmsjo et al. |
| 2013/0039848 A1 | 2/2013 | Bradbury et al. |
| 2013/0045182 A1 | 2/2013 | Gong et al. |
| 2013/0060230 A1 | 3/2013 | Capistron et al. |
| 2013/0079421 A1 | 3/2013 | Aviv et al. |
| 2013/0108574 A1 | 5/2013 | Chevalier et al. |
| 2013/0184660 A1 | 7/2013 | Swiss et al. |
| 2013/0225778 A1 | 8/2013 | Goodrich et al. |
| 2014/0039459 A1 | 2/2014 | Folk et al. |
| 2014/0056806 A1 | 2/2014 | Vernengo et al. |
| 2014/0107251 A1 | 4/2014 | Cruise et al. |
| 2014/0171907 A1 | 6/2014 | Golzarian et al. |
| 2014/0274945 A1 | 9/2014 | Blaskovich et al. |
| 2014/0277057 A1 | 9/2014 | Ortega et al. |
| 2015/0290344 A1* | 10/2015 | Alexis ................. A61K 49/0442 424/9.451 |
| 2016/0243157 A1 | 8/2016 | Cruise et al. |
| 2017/0216484 A1 | 8/2017 | Cruise et al. |
| 2017/0274101 A1* | 9/2017 | Hainfeld ............... A61K 9/5146 |
| 2018/0055516 A1 | 3/2018 | Baldwin et al. |
| 2018/0200288 A1 | 7/2018 | Cruise et al. |
| 2019/0134078 A1 | 5/2019 | Cruise et al. |

FOREIGN PATENT DOCUMENTS

| | | |
|---|---|---|
| CN | 102107025 B | 5/2014 |
| EP | 1599258 B1 | 8/2008 |
| EP | 1601392 B1 | 4/2009 |
| EP | 1558299 B1 | 12/2012 |
| JP | 05-057014 | 3/1993 |
| JP | 1993253283 A | 10/1993 |
| JP | 11-166018 | 6/1999 |
| WO | 2004/073843 A1 | 9/2004 |
| WO | 2005/013810 A2 | 2/2005 |
| WO | 2006/095745 A1 | 9/2006 |
| WO | 2008/118662 A2 | 10/2008 |
| WO | 2011/110589 A1 | 9/2011 |
| WO | 2012/025023 A1 | 3/2012 |
| WO | 2012/088896 A1 | 7/2012 |
| WO | 2012/171478 A1 | 12/2012 |
| WO | 2014/152488 A2 | 9/2014 |
| WO | 2019/074965 A1 | 4/2019 |

OTHER PUBLICATIONS

Dudeck O, Jordan O, Hoffmann KT, et al. Embolization of experimental wide-necked aneurysms with iodine-containing polyvinyl alcohol solubilized in a low-angiotoxicity solvent. AJNR Am J Neuroradiol. 2006;27(9):1849-1855.

Dudeck O, Jordan O, Hoffmann KT, et al. Organic solvents as vehicles for precipitating liquid embolics: a comparative angiotoxicity study with superselective injections of swine rete mirabile. AJNR Am J Neuroradiol. 2006;27(9):1900-1906.

(56) References Cited

OTHER PUBLICATIONS

He et al., Material properties and cytocompatibility of injectable MMP degradable poly(lactide ethylene oxide fumarate) hydrogel as a carrier for marrow stromal cells. Biomacromolecules, vol. 8, pp. 780-792 (2007).
Levasque et al., Synthesis of enzyme-degradable, peptide-cross-linked dextran hydrogels. Bioconjugate Chemistry, vol. 18, pp. 874-885 (2007).
Moss et al., Solid-Phase synthesis and kinetic characterization of fluorogenic enzyme-degradable hydrogel cross-linkers. Biomacromolecules, vol. 7, pp. 1011-1016 (2006).
Onyx Liquid Embolic System Onyx HD-500, Instructions for Use, ev3 Endovascular, Inc., Nov. (2007).
Supplementary European Search Report dated Sep. 26, 2016 for European Patent Application No. 13846860.8 filed on Oct. 15, 2013.
Takao H, Murayama Y, Yuki I, et al. Endovascular treatment of experimental aneurysms using a combination of thermoreversible gelation polymer and protection devices: feasibility study. Neurosurgery. 2009;65(3):601-609.
Jayakrishnan et al., Synthesis and polymerization of some iodine-containing monomers for biomedical applications. Journal of Applied Polymer Science, vol. 44, pp. 743-748 (1992).
International Search Report and Written Opinion, dated Dec. 31, 2018, for International Application No. PCT/US2018/055074.
U.S. Appl. No. 16/287,797, filed Feb. 27, 2019.
Wikipedia, "Isotopes of Iodine" Version: Jun. 15, 2017, Retrieved: Nov. 26, 2018 (https://en.wikipedia.org/w/index.php?title=isotopes_of_iodine&oldid=785724472), p. 2, para 7.
Arslan et al., Use of 4-vinylpyridine and 2-hydroxyethylmethacrylate monomer mixture grafted poly(ethylene terephthalate) fibers for removal of congo red from aqueous solution. E-Polymers, vol. 8, Issue 1, 016, pp. 1-15 (2008).
Shin et al., Inverse opal pH sensors with various protic monomers copolymerized with polyhydroxyethylmethacrylate hyrdrogel. Analytica Chimica Acta, 752:87-93 (2012).
Yi et al., Ionic strength/temperature-induced gelation of aqueous poly(N-isopropylacrylamide-co-vinylimidazole) solution. Macromol. Symp. 207, pp. 131-137 (2004).
Kocer et al., Preliminary experience with precipitating hydrophobic injectable liquid in brain arteriovenous malformations. Diagn Interv Radiol, 22:184-189 (2016).

\* cited by examiner

RADIOACTIVE LIQUID EMBOLIC

CROSS REFERENCE TO RELATED APPLICATIONS

This application claims the benefit of U.S. Provisional Patent Application No. 62/569,941, filed Oct. 9, 2017, the entire disclosure of which is incorporated herein by reference.

FIELD

Described herein generally are liquid embolic and polymer particle preparations and medical treatment methods using those preparations.

SUMMARY

Described herein generally are liquid embolic preparations and medical treatment methods using those preparations. In some embodiments, the preparations or solutions can transition from a liquid to a solid for use in the embolization of arteriovenous malformations (AVM's) and solid tumors. The preparations can include biocompatible polymers with covalently bound radioactive iodine isotopes and a non-physiological solution.

Liquid embolics are introduced through a microcatheter in the liquid state and transition to the solid state once in the body. The transition is generally controlled either by reaction or precipitation. For the materials functioning by reaction, the materials are introduced in a liquid state and undergo a chemical reaction to transition to a solid. For the materials functioning by precipitation, the materials are introduced in a non-physiological condition and transition to a solid upon exposure to physiological conditions. Non-physiological conditions include water miscible organic solvents, temperature, and pH.

Some embodiments are directed to liquid embolic formulations that can be deployed into the vasculature using standard practices and microcatheters/catheters to occlude blood flow. In some embodiments, the liquid embolic formulations are comprised of a biocompatible polymer with biostable or biodegradable linkages to aromatic rings containing a plurality of iodine, wherein some of the iodine atoms are stable and some are radioactive and a water miscible solvent that dissolves the biocompatible polymer.

In one embodiment, the liquid embolic polymer can include 2-oxo-2-(1-oxo-1-(1-oxo-1-(2,4,6-triiodophenoxy)propan-2-yloxy)propan-2-yloxy)ethoxy)ethyl acrylate and hydroxyethyl methacrylate. In some embodiments, the liquid embolic polymer is that polymer sold under the name PHIL by MicroVention, Inc.

In one embodiment, the biodegradable linkage is susceptible to breakage via hydrolysis. In another embodiment, the biodegradable linkage is susceptible to breakage via enzymatic action. In another embodiment, the linkage is biostable and/or substantially biostable. Biostable can be non-biodegradable.

In one embodiment, the stable iodine isotope is $^{127}$I and the radioactive iodine isotope is $^{123}$I, $^{124}$I, $^{125}$I, or $^{131}$I. In one embodiment, the radioactive iodine isotope is $^{123}$I. In one embodiment, the radioactive iodine isotope is $^{124}$I. In one embodiment, the radioactive iodine isotope is $^{125}$I. In one embodiment, the radioactive iodine isotope is $^{131}$I.

In some embodiments, the polymer particles or liquid embolic polymers described herein can include folic acid or a derivatized version thereof.

DETAILED DESCRIPTION

Liquid embolic preparations are described. In some embodiments, medical treatment methods using the liquid embolic preparations are described.

In general terms, the liquid embolic preparation includes (i) a biocompatible polymer with an aromatic ring with a plurality of iodine atoms coupled via biodegradable or biostable linkages and (ii) a water miscible solvent that dissolves the biocompatible polymer.

In some embodiments, a function of the liquid embolic polymer is to solidify in the vasculature or other anatomical structure when coming in contact with blood or other physiological fluid to occlude the vessel or structure and to permit visualization of the polymer when imaged using medically relevant techniques. The liquid embolic polymer's solubility is achieved with the judicious selection of the composition of the polymer to ensure that it is essentially insoluble at physiological conditions. The liquid embolic polymer includes and/or is a reaction product of a prepolymer solution including monomers containing visualization species and optionally other monomers. The ratio of monomers with monomers containing visualization species and other monomers is dependent on the structure of the monomers and is best determined experimentally.

The monomer or monomers with visualization species can impart visibility of the liquid embolic polymer when imaged using a medically relevant imaging technique such as fluoroscopy or computed tomography. Characteristic features of the monomers with visualization species are cores that are visible under medically relevant imaging techniques and a polymerizable moiety attached to the core with a biodegradable linkage.

Visualization of the polymer under fluoroscopy and CT imaging can be imparted by the use of monomers with cores containing iodine, particularly aromatic rings with a plurality of iodine atoms. In one embodiment, a core containing iodine is triiodophenol. Concentrations of iodine to render the liquid embolic visible using fluoroscopy or CT imaging can range from 20% to 50% w/w of the liquid embolic solution.

Polymerizable moieties can include those that permit free radical polymerization, including acrylates, methacrylates, acrylamides, methacrylamides, vinyl groups, and derivatives thereof. Alternatively, other reactive chemistries can be employed to polymerize the liquid embolic polymer, i.e. nucleophile/N-hydroxysuccinimide esters, nucleophile/halide, vinyl sulfone/acrylate or maleimide/acrylate. In some embodiments, polymerizable moieties are acrylates and acrylamides.

Biodegradable linkages permit the separation of the visualization core from the polymer. After separating from the polymer, the core is removed by diffusion or the cells comprising the foreign body response to the polymer. Biodegradable linkages can be separated into two types, those susceptible to hydrolysis and those susceptible to enzymatic action. Linkages susceptible to hydrolysis are generally esters or polyesters. Ester can be introduced by reacting hydroxyl groups with strained anhydrides, such as succinic or glutaric anhydride, or cyclic esters, such as lactide, glycolide, ε-caprolactone, and trimethylene carbonate. The rate of degradation can be controlled by the selection of the ester and the number of the esters inserted into the biodegradable linkages. Linkages susceptible to enzymatic action can generally be peptides that are degraded by particular enzymes, such as matrix metalloproteinases, collagenases, elastases, cathepsin. Peptide sequences degraded by matrix metalloproteinases can include Gly-Pro-Gln-Gly-Ile-Ala-Ser-Gln, Gly-Pro-Gln-Gly\Pro-Ala-Gly-Gln, Lys-Pro-Leu-Gly-Leu-Lys-Ala-Arg-Lys, Gly-Pro-Gln-Ile-Trp-Gly-Gln, and Gln-Pro-Gln-Gly-Leu-Ala-Lys. Peptide sequences degraded by cathepsin include Gly-Phe-Gln-Gly-Val-Gln-Phe-Ala-Gly-Phe, Gly-Phe-Gly-Ser-Val-Gln-Phe-Ala-Gly-Phe, and Gly-Phe-Gly-Ser-Thr-Phe-Phe-Ala-Gly-Phe. Peptide sequences degraded by collagenase include Gly-Gly-Leu-Gly-Pro-Ala-Gly-Gly-Lys and Ala-Pro-Gly-Leu. Peptide sequences degraded by papain include Gly-Phe- Leu-Gly. Peptide sequences degraded by caspase-3 include Asp-Glu-Val-Asp-Thr. The rate of degradation can be controlled by the peptide sequence selection.

Other monomers that can be used can have two characteristic features, namely containing a polymerizable moiety and having a structure that is conducive to the desired solubility characteristics. Preferred polymerizable moieties can be those that permit free radical polymerization, including acrylates, methacrylates, acrylamides, methacrylamides, vinyl groups, and derivatives thereof. Alternatively, other reactive chemistries can be employed to polymerize the liquid embolic polymer, i.e. nucleophile/N-hydroxysuccinimide esters, nucleophile/halide, vinyl sulfone/acrylate or maleimide/acrylate. In some embodiments, polymerizable moieties include acrylates and acrylamides. In general, the other monomer can compensate for the monomers with visualization species. If a prepared polymer is too hydrophobic for dissolution in water miscible solvent, more hydrophilic monomers can be introduced to alter the solubility. If a prepared polymer is too hydrophilic and is soluble in water, more hydrophobic monomers can be introduced to alter the solubility. Other monomers can include hydroxyethyl methacrylate, t-butyl acrylate, t-butyl acrylamide, n-octyl methacrylate, and methyl methacrylate.

In some embodiments, liquid embolic polymers can be polymerized from solutions of monomers with visualization species and optionally other monomers. The solvent used to dissolve the monomers can be any solvent that dissolves the desired monomers. Preferred solvents include methanol and acetonitrile. In other embodiments, the solvent can be dimethylsulfoxide (DMSO) or tetrahydrofuran (THF). In some embodiments, the solvent can be water.

Polymerization initiators can be used to start the polymerization of the monomers in the solution. The polymerization can be initiated by reduction-oxidation, radiation, heat, or any other known method. Radiation cross-linking of the prepolymer solution can be achieved with ultraviolet light or visible light with suitable initiators or ionizing radiation (e.g. electron beam or gamma ray) without initiators. Polymerization can be achieved by application of heat, either by conventionally heating the solution using a heat source such as a heating well, or by application of infrared light to the prepolymer solution.

In some embodiments, the polymerization initiator is azobisisobutyronitrile (AIBN) or a water soluble AIBN derivative (2,2'-azobis(2-methylpropionamidine) dihydrochloride). Other initiators can include AIBN derivatives, including, but not limited to 4,4'-azobis(4-cyanovaleric acid, and other initiators such as N,N,N',N'-tetramethylethylenediamine, ammonium persulfate, benzoyl peroxides, and combinations thereof, including azobisisobutyronitriles. In some embodiments, initiator concentrations can be less than about 0.5% w/w of the prepolymer solution. The polymerization reaction can be run at elevated temperatures, such as about 80° C. After the polymerization is completed, the liquid embolic polymer can be recovered by precipitation in a non-solvent and dried under vacuum.

In one embodiment, the liquid embolic polymer can include 2-oxo-2-(1-oxo-1-(1-oxo-1-(2,4,6-triiodophenoxy)propan-2-yloxy)propan-2-yloxy)ethoxy)ethyl acrylate and hydroxyethyl methacrylate. In some embodiments, the liquid embolic polymer is that polymer sold under the name PHIL by MicroVention, Inc.

The substitution of radioactive iodine for stable iodine can be performed at any of the steps in the synthetic procedure. In one embodiment, substitution of radioactive iodine for stable iodine can occur after the conclusion of the preparation of the liquid embolic polymer. After the liquid embolic polymer has been prepared, it is re-dissolved in dimethyl sulfoxide and the sodium salt of the radioactive iodine is added. After the sodium salt has been completely dissolved, 30% hydrogen peroxide in water is added. The reaction solution can be optionally heated to facilitate the substitution. When the reaction is complete, the liquid embolic polymer is purified with repeated precipitation in water and dissolution in dimethyl sulfoxide.

In another embodiment, the substitution can be performed on the monomer containing a polymerizable moiety with a biostable or biodegradable linkage to an aromatic ring containing a plurality of iodine atoms. The same reaction procedure as described for the liquid embolic polymer may be used for the monomer.

Embodiments described herein can use iodine radioisotopes that include $^{123}I$, $^{124}I$, $^{125}I$, and $^{131}I$. Each isotope has distinct properties that ablate tissue and permit imaging. In one embodiment, the isotope used is $^{131}I$ due to its destructive beta emissions, gamma emissions that can be used for medical imaging, and short half-life.

In some embodiments, polymers described herein can include a monomer including at least one iodine. Examples of iodinated monomers include, but are not limited to triiodophenol, 1-((2-(methacryloyloxy)ethoxy)carbonyloxy) ethyl-3,5-diacetamido-2,4,6-triiodobenzoate, and 2-oxo-2-(1-oxo-1-(1-oxo-1-(2,4,6-triiodophenoxy)propan-2-yloxy) propan-2-yloxy)ethoxy)ethyl acrylate. However, in some embodiments, any monomer including iodine can be used.

In some embodiments, a polymer particle or liquid embolic polymer includes triiodophenol and 3,6-dimethyl-1,4dioxane-2,5 dione.

In some embodiments, a polymer particle or liquid embolic polymer includes 2-oxo-2-(1-oxo-1-(1-oxo-1-(2,4,6-triiodophenoxy)propan-2-yloxy)propan-2-yloxy)ethoxy)ethyl acrylate and hydroxyethyl methacrylate.

In some embodiments, a polymer particle or liquid embolic polymer includes triiodophenol and hydroxyethyl methacrylate.

In some embodiments, a polymer particle or liquid embolic polymer includes a triiodophenol with a chain extended lactide units and capped with an acrylate.

In some embodiments, a radioactive iodine salt can be used with hydrogen peroxide to exchange iodine atoms on an iodinated monomer with radioactive iodine. In some embodiments, the salt is a sodium salt.

In some embodiments, the polymer particles can have a radioactive yield. This radioactive yield can be developed under homogenous conditions. Therein, the radioactive yield can be between about 1% and about 15%, between about 1% and about 5%, between about 5% and about 20%, between about 10% and about 15%, between about 5% and about 15%, between about 10% and about 12%, or between about 5% and about 30%.

In other embodiments, radioactive yield can be developed under heterogeneous conditions. Therein, the radioactive yield can be between about 1% and about 75%, between about 50% and about 75%, between about 50% and about 60%, between about 70% and about 75%, between about 70% and about 80%, between about 40% and about 45%, or between about 70% and about 75%.

In some embodiments, the polymer particles can have a radiochemical purity of between about 50% and about 90%, between about 70% and about 90%, between about 70% and about 75%, between about 85% and about 90%, between about 80% and about 90%, greater than about 70%, greater than about 80%, greater than about 85%, greater than about 90%.

In some embodiments, the liquid embolic polymers can have a radioactive yield. This radioactive yield can be developed under homogenous conditions. Therein, the radioactive yield can be between about 1% and about 15%, between about 1% and about 5%, between about 5% and about 20%, between about 10% and about 15%, between about 5% and about 15%, between about 10% and about 12%, or between about 5% and about 30%.

In other embodiments, radioactive yield can be developed under heterogeneous conditions. Therein, the radioactive yield can be between about 1% and about 75%, between about 50% and about 75%, between about 50% and about 60%, between about 70% and about 75%, between about 70% and about 80%, between about 40% and about 45%, or between about 70% and about 75%.

In some embodiments, the liquid embolic polymers can have a radiochemical purity of between about 50% and about 90%, between about 70% and about 90%, between about 70% and about 75%, between about 85% and about 90%, between about 80% and about 90%, greater than about 70%, greater than about 80%, greater than about 85%, greater than about 90%.

The water miscible solvent is used to dissolve of the liquid embolic polymer. Concentrations of the liquid embolic polymer in the aqueous solution can range from about 2.5% to about 25%, more preferably between about 5% and about 15%.

In some embodiments, the liquid embolic device is prepared by dissolving the liquid embolic polymer in the water miscible solvent, adding to an appropriate vial or other container, and capping the vial. A preferred method of sterilization before use is autoclaving.

The liquid embolic formulation is removed from the vial using a needle and syringe. To prevent premature liquid embolic polymer deposition, the delivery catheter is flushed with a bolus of the same water miscible solvent as was used to dissolve the liquid embolic polymer. This flushing prevents clogging of the delivery catheter with the liquid embolic polymer. The syringe containing the liquid embolic formulation is then connected to the proximal end of delivery catheter, such as a microcatheter, cannula, or the like, positioned in the desired vascular or other anatomic site.

As the liquid embolic formulation is injected, it pushes the water miscible solvent flushing solution out of the microcatheter. The progress of the liquid embolic formulation inside the delivery catheter can be observed using an imaging technique compatible with the visualization species selected. With continued injection, the liquid embolic formulation enters the target delivery site. The solidified liquid embolic polymer provides long-term occlusion of the target site. Over time, the biodegradable linkages binding the visualization species to the liquid embolic polymer are broken and the visualization of the liquid embolic polymer is diminished.

In other embodiments, radioactive iodine-containing polymers as described herein can be used to target cancer at the cellular level. In some embodiments, these polymers can be those described in the Examples.

The radioactive iodine-containing polymers can be formed into particles. These particles can have diameters of about 10 nm to about 50 nm, about 10 nm to about 40 nm, about 10 nm to about 30 nm, about 10 nm to about 20 nm, about 20 nm to about 50 nm, about 30 nm to about 50 nm, about 40 nm to about 50 nm, or about 20 nm to about 40 nm. Many different methods can be used to prepare particles from the herein described iodine-containing polymers. In one embodiment, particles can be formed by forcing an iodine-containing polymer through a nozzle at high pressure in a medium such as air, water, or oil. In some embodiments, the nozzle can be like the nozzle used for ink jet printing. The resulting particles may then be separated by size using, for example, electrostatic techniques, centrifuge, filtering, sieving, or a combination thereof.

The polymer particles or liquid embolic particles described herein can be covalently functionalized with folic acid.

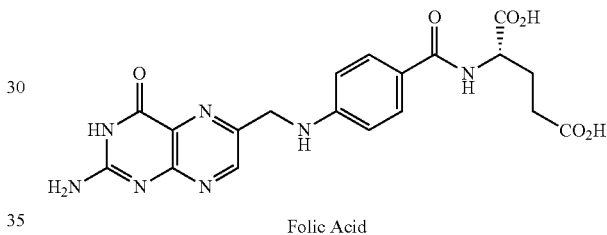

Folic Acid

In one embodiment, folic acid can be functionalized using poly(ethylene glycol). In one embodiment, a functionalized folic acid can have a structure

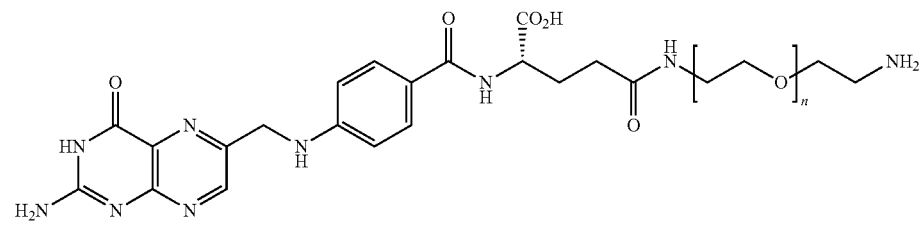

wherein n is 0-100.

In another embodiment, a functionalized folic acid can have a structure

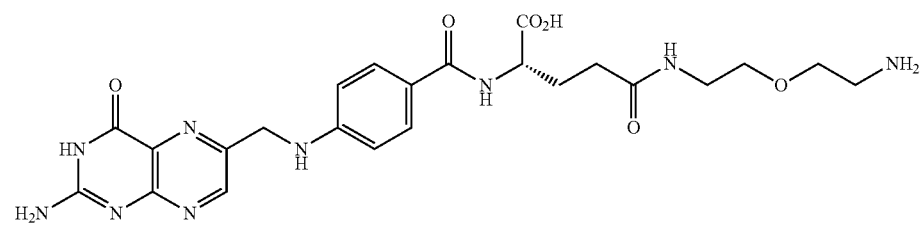 [SMILES: NCCOCCNC(=O)CC[C@H](NC(=O)c1ccc(NCc2cnc3nc(N)[nH]c(=O)c3n2)cc1)C(=O)O]

In some embodiments, a functionalized folic acid can react with hydroxyl groups on an embolic or other particle.

In an alternative embodiment, folic acid may be bonded to the polymer structure at the time of synthesis and formed into particles by the methods described.

Folic acid (vitamin B9, folate) can be used for cell division. Therefore, rapidly dividing cells such as cancer cells overexpress folate receptors on their surface. In some embodiments, the radioactive polymer with functionalized folic acid can be taken up by folate receptors on the cancer cells. This can make radiotherapy more targeted to cancer cells relative to normal cells. Depending on the dose, the radiation may be used therapeutically to destroy or damage the cancerous cells, or may be used as a diagnostic marker at lower radiation dose.

To deliver the radioactive particles functionalized with folic acid, the particles may be placed in a suspension with a biocompatible liquid such as lipiodol, contrast, saline solution, or the like. The suspension may require mixing or agitation prior to use depending on the size and number of particles. In some embodiments, the suspension may be directly injected into a tumor through a catheter, microcatheter, syringe/needle, or the like. In another embodiment, the suspension may be infused into the bloodstream as a chemotherapy agent.

Once injected at either a therapeutic or a diagnostic dose, an external monitoring instrument, such as a gamma camera, may be used to locate areas within the body of high uptake of particles. This method can be used to detect, for example, previously unknown metastases. Since it acts at the cellular level, this method would be sensitive to even metastases of only a few cells outside the original tumor location.

In some embodiments, a container is provided including a therapeutic amount of polymer polymers functionalized with folic acid. In some embodiments, the container can be a vial, a bottle, a syringe, an IV bag, an IV bottle, or the like. In some embodiments, the container can be any container that can be used to transfer the polymer functionalized with folic acid into a patient using a medically relevant method.

In some embodiments, methods of treatment using the herein described radioactive polymer particles are described. Methods can include injecting a solution including the polymer particles into a treatment site. The treatment site can be a vessel. In other embodiments, the treatment site can be any lumen in need of treatment.

In some embodiments, methods of treatment using the herein described radioactive liquid embolic polymers are described. Methods can include injecting a solution including the dissolved liquid embolic polymer particles into a treatment site. Upon encountering a condition, the liquid embolic polymers precipitate. The condition can be a change in pH, a change in temperature, or a change in solubility. The treatment site can be a vessel. In other embodiments, the treatment site can be any lumen in need of treatment.

Polymer particles and/or liquid embolic polymers described herein can be delivered using a needle and syringe and/or injected through a catheter or microcatheter.

Kits including the herein described polymer particles are also described. Kits can include a container including a solution. The solution can include a radioactive polymer particle as described herein. The kit can include instructions for use. The kits can also include a syringe or a catheter or microcatheter for delivery.

Kits including the herein described liquid embolic polymers are also described. Kits can include a container including a solution. The solution can include a radioactive liquid embolic polymer as described herein. The kit can include instructions for use. The kits can also include a syringe or a catheter or microcatheter for delivery.

In some embodiments, the kits can further include a solution used to flush the particle solution or liquid embolic polymer through a catheter or microcatheter.

The container can be a vial, tube, syringe, or the like.

Example 1

Preparation of an Iodine-Containing Monomer

To 250 milliliters of toluene, 15 g triiodophenol, 22.9 g 3,6-dimethyl-1,4-dioxane-2,5 dione, and 25 microliters of stannous octoate were added. The solution was refluxed for 18 hr. After cooling the solution to 25° C., 3 ml acryloyl chloride and 5.2 ml triethylamine dissolved in 50 ml toluene were added. The mixture was stirred for 5 hr, filtered, washed with water, and dried under vacuum.

Example 2

Preparation of an Iodine-Containing Polymer

To 3 milliliters of dimethyl sulfoxide, 1.8 g triiodophenol chain extended with an average of 5 lactide units and capped with an acrylate, 0.2 g of hydroxyethyl methacrylate, and 10 mg of azobisisobutyronitrile were added. Upon complete dissolution of all components, the solution was placed at 80° C. for 4 hours. After cooling to room temperature, the polymer was recovered by precipitation in ethyl ether and dried under vacuum.

Example 3

Exchanging Iodine on an Iodine-Containing Polymer (Prophetic)

To a dimethyl sulfoxide solution of the iodine-containing polymer of Example 2, $Na^{131}I$ is added with stirring. After the $Na^{131}I$ is completely dissolved, hydrogen peroxide (30% in aqueous solution) is added. The reaction is optionally heated to facilitate the exchange process. After 10 min of reaction time (or longer as needed), the DMSO solution is poured over distilled water to precipitate the iodine-containing polymer. The precipitate is filtered and subsequently redissolved in DMSO and reprecipitated in DI water twice more. The solid is then lyophilized to remove water and obtain the product as a solid.

Example 4

Preparation of Liquid Embolic Formulation

To 9 g of dimethyl sulfoxide, one gram of the polymer of Example 3 was added. The liquid embolic formulation was then aliquoted into vials and capped. The vials were autoclaved at 121° C. for 15 minutes.

Example 5

Electrophilic Radioiodination of PHIL with $Na^{125}I$ Under Homogenous Conditions An excess equivalent of $Na^{125}I$ (dissolved in $10^{-5}$ M NaOH solution, pH=8) is added to a solution of 1000 ppm liquid embolic including 2,4,6-triiodophenyl 5-(2-(2-(acryloyloxy)acetoxy)acetoxy)-2-methyl-4-oxohexanoate and hydroxyethyl methacrylate in tetrahydrofuran (THF). In one embodiment, this liquid embolic is sold under the name PHIL by MicroVention, Inc. After an extend reaction time, e.g. 30 min, 60 min, and 90 min, the reaction is quenched, and the polymer is recovered by precipitation in water. The radioactive yield and the polymer recovery percentage are listed in Table 1.

TABLE 1

Summary of the yields and conditions of liquid embolic electrophilic radioiodination.

| Solvent Used | Reaction time | Radioactive yield | Polymer recovery percentage |
|---|---|---|---|
| THF | 90 min | 11% | 3.8% |
| DMSO | 90 min | 2.5% | 6.0% |

Example 6

Electrophilic Radioiodination of PHIL with Na$^{125}$I Under Heterogeneous Conditions A solution of Na$^{125}$I (101.72 mCi/mL) in 0.1% TFA in CH$_3$CN is added to a solution of liquid embolic polymer including 2,4,6-triiodophenyl 5-(2-(2-(acryloyloxy)acetoxy) acetoxy)-2-methyl-4-oxohexanoate and hydroxyethyl methacrylate (50-200 μg) in dichloromethane (80-120 μL). In one embodiment, this liquid embolic is sold under the name PHIL by MicroVention, Inc. To this solution, 50 μg of iodogen (1 mg/mL in DCM) is added. The solution is left to react at room temperature for 5-15 min. The radioactive yield is not benefitted from extending the reaction time to longer than 15 min. The reaction is quenched with sodium metabisulphite (10 mg/mL in PBS). The reaction is centrifuged at 2,000 rpm for 15 min to separate the pellet from the supernatant. The pellet is washed twice with dichloromethane. With this method, it is estimated that an average of 2.7 MBq radioactivity was obtained from 100 μg liquid embolic polymer starting material.

Example 7

Electrophilic Radioiodination of PHIL with Na$^{125}$I Under Heterogeneous Conditions with Iodogen on a Milligram Scale Na$^{125}$I aliquots (2 mCi-5 mCi) were evaporated to dryness under the stream of sterile N$_2$. CH$_2$Cl$_2$ containing 0.1% TFA (v/v) was added to the Na$^{125}$I residue, vortexed briefly and transferred into the radioiodination tube containing the suspension of PHIL in CH$_2$Cl$_2$. Iodogen was added and the radioiodination mixture was vortexed (~1 min) and sonicated (~5 min). CH$_2$Cl$_2$ was removed from the $^{125}$I-PHIL pellet. The pellet was washed with 2×0.4 mL CH$_2$Cl$_2$, 1×1 mL Na$_2$S$_2$O$_5$ (10 mg/mL water), 1×1 mL distilled H$_2$O and dried under the vacuum. The dry $^{125}$I-PHIL pellet was dissolved in 1 mL THF and subjected to ITLC and TLC analyses. The results are listed in Table 2.

TABLE 2

Summary of the yields and conditions of liquid embolic electrophilic radioiodination using iodogen as the oxidant on a milligram scale.

| Starting material | 50 mg PHIL* | 100 mg PHIL |
|---|---|---|
| Radiochemical yield (%) | 43.9% | 73.8% |
| Specific activity (mCi/mg) | 0.028 mCi/mg PHIL | 0.028 mCi/mg PHIL |
| Radiochemical purity | 73% | 87% |

*results calculated from average of two reactions.

Example 8

Electrophilic Radioiodination of PHIL with Na$^{125}$I Under Heterogeneous Conditions with Chloroamine-T on a Milligram Scale To the radioiodination tube containing the suspension of PHIL in CH$_2$Cl$_2$ and aliquot of Na$^{125}$I in 1×10$^{-5}$ M NaOH was added followed by chloramine-T and CH$_2$Cl$_2$ containing 0.1% TFA (v/v). The reaction mixture was vortexed for ~2 min and sonicated ~5 min. CH$_2$Cl$_2$ layer and the resuspended $^{125}$I-PHIL pellet were washed with 1×1 mL Na$_2$S$_2$O$_5$ (10 mg/mL water). The organic and aqueous layers were removed and the solid residue washed again with 1×1 mL Na$_2$S$_2$O$_5$ (10 mg/mL water) and 2×1 mL distilled H$_2$O. The washed $^{125}$I-PHIL pellet was dried under vacuum. The dry $^{125}$I-PHIL pellet was dissolved in 1 mL THF and subjected to ITLC analyses. From two reactions using 12 mg of PHIL as the starting material, the radiochemical yield was 73.0%, the specific activity was 0.083 (mCi/mg), and the radiochemical purity was 97% (% by ITLC).

Example 9

Coupling Folic Acid to Radio Liquid Embolic

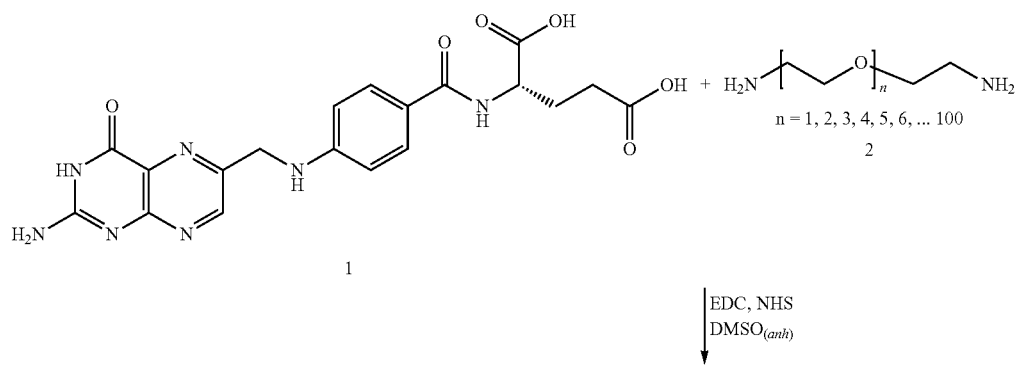

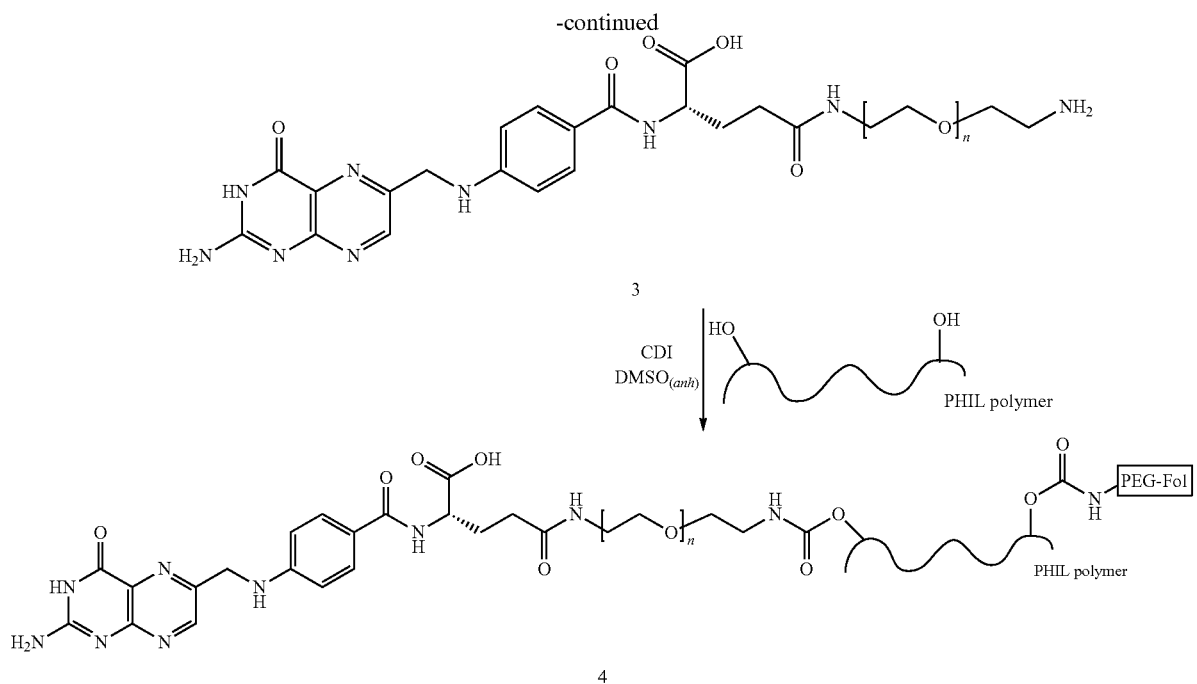

Folic acid (1, 4.41 g, 10 mmol) is dissolved into a mixture of anhydrous dimethyl sulfoxide (DMSO, 100 mL) and triethylamine (TEA, 0.5 mL), and activated by 1-(3-dimethylaminopropyl)-3-ethylcarbodiimide hydrochloride (EDC, 1.9 g, 10 mmol) and N-hydroxysuccinimide (NHS, 1.15 g, 10 mmol) under nitrogen anhydrous conditions for 2 hr at room temperature. One molar equivalent of poly(ethylene glycol) bis(amine) is dissolved in 50 mL of DMSO. Under stirring, the solution of activated folic acid is added dropwise into the solution of poly(ethylene glycol) bis(amine). The resulting mixture is stirred at room temperature for about 24 hr under nitrogen anhydrous condition. The final product 3 is purified by HPLC.

Synthesis of Folate-PEG-PHIL Conjugate (4)

PHIL polymer (0.5 mmol) is dissolved in 50 mL of anhydrous DMSO followed by addition of N,N'-carbonyldiimidazole (CDI, 0.81 g, 5 mmol). The reaction is stirred under anhydrous nitrogen for 4 hr. The Folate-PEG-$NH_2$ (3, 5 mmol) is dissolved in 10 mL of anhydrous DMSO. The resulting solution is added into the PHIL polymer solution dropwise. The reaction mixture is stirred for 6 hr at room temperature. The solution is dried using rotovap and the crude is re-dissolved in DMSO and purified by repeated precipitation in methyl tert-butyl ether to obtain the final product 4.

Example 10

Preparation of Nanoparticles

Nano/micro particles are prepared from the solution prepared in Example 9 using a precipitation procedure. The dimethyl sulfoxide solution is slowly dispersed into water with vigorous agitation. As dimethyl sulfoxide is dispersed within the water and diffuses into the water, small particles of radioactive polymer coupled with folic acid are formed. The particles can be collected and repeatedly washed with centrifugation. Finally, the particles are dried using lyophilization. If smaller particles sizes are required, they may be mechanically milled before being packaged appropriately.

Example 11

Preparation of Nanoparticles

Nano/micro particles are prepared from the solution prepared in Example 9 using an atomization procedure. The dimethyl sulfoxide solution is slowly injected through a heated needle with coaxial gas flow. As the dimethyl sulfoxide is evaporated by the gas, small particles of radioactive polymer coupled with folic acid are formed. The particles can be collected in water and repeatedly washed with centrifugation. Finally, the particles are dried using lyophilization. If smaller particles sizes are required, they may be mechanically milled before being packaged appropriately.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A polymeric composition comprising:
   a biocompatible polymer comprising a reaction product of:
   a first monomer including a polymerizable moiety having a linkage to a visualization agent having at least one aromatic ring, wherein the at least one aromatic ring includes at least one iodine atom, wherein at least one of the at least one iodine atom is a radioactive isotope, and wherein the first monomer is 2,4,6-triiodophenyl 5-(2-(2-(acryloyloxy)acetoxy)acetoxy)-2-methyl-4-oxohexanoate,
   and a second monomer including a polymerizable moiety and at least one hydroxyl group; and
   a non-physiological solution;
   wherein the biocompatible polymer is soluble in the non-physiological solution and insoluble in a physiological solution.

2. The polymeric composition of claim 1, wherein the linkage is biodegradable.

3. The polymeric composition of claim 1, further including folic acid or a functionalized form thereof.

4. The polymeric composition of claim 1, wherein the radioactive isotope is $^{123}I$, $^{124}I$, $^{125}I$, $^{131}I$, or a combination thereof.

5. The polymeric composition of claim 1, wherein the radioactive isotope is $^{123}I$.

6. The polymeric composition of claim 1, wherein the radioactive isotope is $^{124}I$.

7. The polymeric composition of claim 1, wherein the radioactive isotope is $^{125}I$.

8. The polymeric composition of claim 1, wherein the radioactive isotope is $^{131}I$.

9. The polymeric composition of claim 2, further including folic acid or a functionalized form thereof.

10. A polymeric composition comprising:
    biocompatible polymer particles, wherein the polymer particles include a reaction product of:
    a first monomer including a polymerizable moiety having a linkage to a visualization agent having at least one aromatic ring, wherein the at least one aromatic ring includes at least one iodine atom, wherein at least one of the at least one iodine atom is a radioactive isotope, and wherein the first monomer is 2,4,6-triiodophenyl 5-(2-(2-(acryloyloxy)acetoxy)acetoxy)-2-methyl-4-oxohexanoate,
    and a second monomer including a polymerizable moiety.

11. The polymeric composition of claim 10, wherein the linkage is biodegradable.

12. The polymeric composition of claim 10, further including folic acid or a functionalized form thereof.

13. The polymeric composition of claim 10, wherein the radioactive isotope is $^{123}I$, $^{124}I$, $^{125}I$, $^{131}I$, or a combination thereof.

14. The polymeric composition of claim 10, wherein the radioactive isotope is $^{123}I$.

15. The polymeric composition of claim 10, wherein the radioactive isotope is $^{124}I$.

16. The polymeric composition of claim 10, wherein the radioactive isotope is $^{125}I$.

17. The polymeric composition of claim 10, wherein the radioactive isotope is $^{131}I$.

18. The polymeric composition of claim 11, further including folic acid or a functionalized form thereof.

19. A method of embolization, the method including delivering the polymeric composition of claim 1 to a lumen in need thereof.

20. A method of embolization, the method including delivering the polymeric composition of claim 10 to a lumen in need thereof.

* * * * *